United States Patent [19]

Geddes et al.

[11] Patent Number: 5,058,583

[45] Date of Patent: Oct. 22, 1991

[54] MULTIPLE MONOPOLAR SYSTEM AND METHOD OF MEASURING STROKE VOLUME OF THE HEART

[76] Inventors: Leslie A. Geddes, 400 N. River Rd., #1724; Neal E. Fearnot, 3051 Hamilton St., both of West Lafayette, Ind. 47907; Jerry L. Wessale, 2268 Federal Pkwy., Lindenhurst, Ill. 60046

[21] Appl. No.: 553,434

[22] Filed: Jul. 13, 1990

[51] Int. Cl.$^5$ .............................................. A61N 1/00
[52] U.S. Cl. ........................ 128/419 D; 128/419 PG; 128/734; 128/693
[58] Field of Search ........ 128/419 PG, 419 P, 419 D, 128/734, 693

[56] References Cited

U.S. PATENT DOCUMENTS

| | | | |
|---|---|---|---|
| 4,291,699 | 9/1981 | Geddes et al. | 128/419 D |
| 4,303,075 | 12/1981 | Heilman et al. | 128/419 PG |
| 4,535,774 | 8/1985 | Olson | 128/419 PG |
| 4,674,518 | 6/1987 | Salo | 128/695 |
| 4,686,987 | 8/1987 | Salo et al. | 128/419 PG |
| 4,697,591 | 10/1987 | Lekholm et al. | 128/419 PG |
| 4,702,253 | 10/1987 | Nappholz et al. | 128/419 PG |
| 4,721,115 | 1/1988 | Owens | 128/713 |
| 4,730,619 | 3/1988 | Koning et al. | 128/419 PG |
| 4,733,667 | 3/1988 | Olive et al. | 128/419 PG |
| 4,790,318 | 12/1988 | Elmqvist et al. | 128/419 PG |
| 4,805,621 | 2/1989 | Heinze et al. | 128/419 PG |
| 4,823,797 | 4/1989 | Heinze et al. | 128/419 PG |
| 4,840,182 | 6/1989 | Carlson | 128/694 |
| 4,867,160 | 9/1989 | Schaldach | 128/419 PG |
| 4,898,176 | 2/1990 | Petre | 128/642 |
| 4,905,696 | 3/1990 | Amundson et al. | 128/419 PG |
| 4,911,174 | 3/1990 | Pederson et al. | 128/734 |
| 4,951,682 | 8/1990 | Petre | 128/734 |

FOREIGN PATENT DOCUMENTS 0089014 9/1983 European Pat. Off. ..... 128/419 PG

OTHER PUBLICATIONS

Sowton, "Haemodynamic Studies in Patients with Artificial Pacemakers", *British Heart Journal* 26:737-746 (1964).

Benchimol et al., "Effect of Exercise and Isoproterenol on the Cardiovascular Dynamics in Complete Heart Block at Various Heart Rates", *American Heart Journal* 70(3):337-347 (Sep. 1965).

Ross et al., "Effects of Changing Heart Rate in Man by Electrical Stimulation of the Right Atrium", *Circulation* 32:549-558 (1965).

Geddes et al., "Continuous Measurement of Ventricular Stroke Volume by Electrical Impedance", *Cardiovascular Research Center Bulletin* 4(4):118-130 (1966).

(List continued on next page.)

*Primary Examiner*—Francis Jaworski
*Assistant Examiner*—George Manuel
*Attorney, Agent, or Firm*—Woodard, Emhardt, Naughton Moriarty & McNett

[57] ABSTRACT

A multiple monopolar system and method for measuring stroke volume of a patient's heart. An intracardiac impedance catheter is provided with a plurality of monopolar electrodes axially spaced along the surface of its distal end, and is used in conjunction with a distant reference electrode which may, for example, be incorporated into the conductive case of a pacemaker. The proximal end of the catheter is attached to the pacemaker, which, in addition to pulse generator circuitry and circuitry for sensing electrical activity of the heart and for controlling pacing rate, includes a constant-current source for current injection into the volume of blood in the patient's ventricle and an impedance processor for measuring the resultant voltage between one of the monopolar electrodes in the ventricle and the pacemaker case and for calculating stroke volume therefrom. A system and method are also disclosed for generating a three-phase relationship between cardiac output and heart rate for an individual patient at a particular workload, for purposes of determining optimal heart rate, as is a method of using the monopolar electrode configuration to detect ventricular fibrillation.

27 Claims, 3 Drawing Sheets

OTHER PUBLICATIONS

Pitt et al., "Coronary Hemodynamic Effects of Increasing Ventricular Rate in the Unanesthetized Dog", *Circulation Research* XXII:753–761 (Jun. 1968).

Palmer, "Continuous Measurement of Stroke Volume by Electrical Impedance in the Unanesthetized Animal", PhD Thesis, Baylor University, Title page, ii, 44–48, 92–99, Conclusions (Jun., 1970).

Tacker et al., "Optimal Spacing of Right Ventricular Bipolar Catheter Electrodes for Detecting Cardiac Pumping by an Automatic Implantable Defibrillator", *Med. Instrum.* 14:27 (1980).

Baan et al., "Continuous Stroke Volume and Cardiac Output from Intraventricular Dimensions Obtained with Impedance Catheter", *Cardiovasc. Res.* 15:328–334 (1981).

Senda et al., "Assessment of Cardiac Response to Pacing Rate and Work Load with Impedance Cardiography in the Pacemaker Implanted Patients", *Japanese Circulation Journal* 46(8):799 (1982) (Abstract).

Baan et al., "Continuous Measurement of Left Ventricular Volume in Animals and Humans by Conductance Catheter", *Circulation* 70:812–823 (1984).

Geddes et al., "The Exercise-Responsive Cardiac Pacemaker", *IEEE Transactions on Biomedical Engineering* BME 31(12):763–770 (1984).

Fujiyama et al., "Reconsideration of Heart Rate-Cardiac Output Relationships and Resting Cardiac Function in Patients with Brady-Arrhythmias", *Jpn. Heart J.* 25(5):713–723 (Sep. 1984).

Fearnot et al., "Control of Pacing Rate Using Venous Blood Temperature", *39th ACEMB Proceedings* 69–72 (Sep., 1986).

Nappholtz et al., "Electrode Configurations for a Respiratory Impedance Measurement Suitable for Rate Responsive Pacing", *PACE* 9:960–964 (Nov.–Dec. 1986).

Davis et al., "Driving Electrode Configurations in Cardiac Conductance Volumetry", *IEEE Eng. Med. & Med. Biol. Soc. 10th Ann. Conf.* 757–758 (1988).

Boheim et al., "Rate-Responsive Pacemaker with Intracardiac Volume Feedback Control", *Biotronik Pacer–Gram* 5(2) (1988).

Wessale et al., "Cardiac Output Versus Pacing Rate at Rest and with Exercise in Dogs with AV Block", *PACE* 11:575–582 (May, 1988).

Voelz et al., "Analysis of Right-Ventricular Impedance Waveform and its Correlation to Stroke Volume", *PACE* 11:812 (Jun. 1988 Supplement) (Abstract).

Yeh et al., "Right Ventricular Stroke Volume Assessment Using an Impedance Catheter", *JACC* 11(2):166A (1988) (Abstract).

Geddes, "The Next Generation Pacemaker", *PACE* (Feb. 1990).

Wessale et al., "Stroke Volume and the Three-Phase Cardiac Output-Rate Relationship with Ventricular Pacing", *PACE* 13:673–680 (May, 1990).

MULTIPLE MONOPOLAR SYSTEM AND METHOD OF MEASURING STROKE VOLUME OF THE HEART

BACKGROUND OF THE INVENTION

This invention relates to systems and method of measuring the stroke volume of a heart, and more particularly to such systems and methods based on measurement of intracardiac impedance.

In recent years, a number of attempts have been made to measure left or right ventricular stroke volume (SV) by intracardiac electrical impedance change ($\Delta Z$). Examples of the foregoing are disclosed in the following U.S. patents:

| Pat. No. | Inventor | Issue Date |
| --- | --- | --- |
| 4,898,176 | Petre | Feb. 6, 1990 |
| 4,840,182 | Carlson | Jun. 20, 1989 |
| 4,823,797 | Heinze et al. | Apr. 25, 1989 |
| 4,721,115 | Owens | Jan. 26, 1988 |
| 4,686,987 | Salo et al. | Aug. 18, 1987 |
| 4,674,518 | Salo | Jun. 23, 1987 |
| 4,535,774 | Olson | Aug. 20, 1985 |
| 4,303,075 | Heilman et al. | Dec. 1, 1981 |
| 4,291,699 | Geddes et al. | Sep. 29, 1981 |

Impedance catheters of the type disclosed is such patents typically have pairs of electrodes on their distal ends in a bipolar or tetrapolar configuration. Early work on the use of catheter-based electrodes was performed by Palmer at Baylor University and reported in 1970 in a PhD thesis entitled "Continuous Measurement of Stroke Volume by Electrical Impedance in the Unanesthetized Animal." Palmer employed the bipolar method, which involves injection of a constant current between two electrodes disposed within a chamber of a heart, e.g., one of the ventricles, with the resultant voltage between the electrodes being measured as an indication of the impedance of the blood in the portion of the ventricle between the electrodes. The tetrapolar configuration also involves establishing a current flow between two source electrodes disposed in the ventricle, but voltage is measured between an inner pair of electrodes disposed between the two source electrodes. The principle in either case is that the current flowing between the catheter electrodes is confined largely to the ventricle in which the catheter is located because the resistivity of the ventricular wall and septum is appreciably higher than that of blood. As a first approximation, the ventricle may be modeled as a cylinder with a sensing electrode at each end. The impedance between the electrodes is inversely proportional to the volume of blood between the sensing electrodes and directly proportional to the blood resistivity. At end diastole the ventricular volume is the highest during the cardiac cycle and the impedance is lowest, whereas at end systole the ventricular volume is the lowest and the impedance is highest, the impedance change ($\Delta Z$) being related to stroke volume (SV).

However, with a bipolar or tetrapolar electrode system, the current distribution between the source electrodes is not uniform. A large portion of the current hugs the catheter and relatively little spreads to intercept the free wall, as shown in FIG. 1 for bipolar electrodes 1a and 1b in the right ventricle (RV). It is difficult to obtain adequate current spread by increasing the electrode spacing because of artifacts produced by the tricuspid valve and papillary muscles. Moreover, if the electrodes come close to the septum or ventricular walls, the relationship between $\Delta Z$ and SV is different, making it difficult to obtain a $\Delta Z$ that bears a constant relationship to SV.

A significant amount of effort has been put into improving the accuracy of the bipolar method. Baan et al., as reported in "Continuous Stroke Volume and Cardiac Output from Intraventricular Dimensions Obtained with Impedance Catheter," *Cardiovasc. Res.* 15:328–334 (1981), and "Continuous Measurement of Left Ventricular Volume in Animals and Humans by Conductance Catheter," *Circulation* 70:812–823 (1984), modeled the ventricle as a column of stacked cylinders each defined by a pair of sensing electrodes, and added the individual cylinder volumes to obtain total ventricular volume. Similar techniques are described in the above-referenced patents to Salo, Owens, Carlson and Petre, along with proposals for solution of various problems associated with the method. Salo sought to solve the problem of nonuniform current density by using extrapolation to compute an impedance value equivalent to what would be measured with drive electrodes spaced an infinite distance apart, from which distance the electric field lines between the electrodes would theoretically be straight and parallel. Regarding the number of required electrodes with this technique, Owens indicates that as few as four would be sufficient for measurement of relative stroke volume, although accompanying thermal dilution measurements would be important in such cases, but that ten electrodes would be more appropriate for assessment of absolute stroke volume. Owens and Peter both disclose stiffening members intended to space the electrodes away from endocardial tissue. Carlson introduced an algorithm designed to eliminate overestimation of stroke volume caused by parallel conductance of the heart wall and surrounding tissue. The algorithm requires measurements at two different frequencies and solution of simultaneous equations at the two frequencies to cancel out parallel conductance terms.

We believe that a catheter-borne, monopolar electrode offers significant advantages over all known bipolar, tripolar and tetrapolar electrode configurations, including, among other things, a more constant relationship with stroke volume. In contrast to the bipolar and tetrapolar methods described above, the monopolar method involves use of a single electrode at the site of the impedance change, and an indifferent or reference electrode distant from the site of activity. The conductive case of a pacemaker implanted in a patient's chest may serve as the reference electrode. A constant current is injected between the active and reference electrodes and the resultant voltage is measured between the same two electrodes. Theoretically, current spreads radially from the active electrode, as shown in FIG. 2 for a single monopolar electrode 2, such that there is increased opportunity for the current to intercept the free wall, thereby providing a more constant relationship between $\Delta Z$ and SV. A study in our laboratory has shown that the impedance measured in the foregoing manner is insensitive to the location of a reference electrode on the chest.

Monopolar electrode configurations appear in the above-referenced Heinze et al. patent in the context of stroke volume measurement for pacemaker control, in U.S. Pat. Nos. 4,697,591 and 4,790,318 to Leckholm et al. and Elmqvist et al., respectively, in the context of pacemakers controlled by a respiratory signal, and in U.S. Pat. No. 4,805,621 to Heinze et al. in the context of a pacemaker controlled by an impedance signal component directly related to metabolism and not influenced by respiration or stroke volume. Davis et al., in an article entitled "Driving Electrode Configurations in Cardiac Conductance Volumetry," in *IEEE Eno. Med. & Med. Biol. Soc.* 10th Ann. Conf. 757–758 (1988), concluded from theoretical studies based on a spherical model of the ventricle that a configuration having a monopole current source at the origin and a sink at infinity, with the potential sensed at an arbitrary distance from the source, has advantages over bipolar configurations for measuring stroke volume. Mentioned as a possibility in the article is a volumetric sensor with sensing electrodes placed spherically about a monopole source within the ventricle.

A number of disadvantages remain with all available configurations and techniques for measurement of stroke volume based on intracardiac impedance. Large artifacts can be encountered with any catheter-electrode system when a current-injecting electrode comes close to the ventricular walls, valves or septum. Furthermore, even with a monopolar electrode configuration, the relationship between $\Delta Z$ and SV is not linear over a wide range of stroke volumes, although a linear relationship appears to hold for a smaller range of volumes. Electrode position in the ventricle also appears to be important for reasons unrelated to artifacts. There is not necessarily any one position that is optimal for stroke volume measurements in all patients. An optimal position for one patient may be unsuitable for another, particularly considering that the ventricles often do not contract uniformly in diseased hearts, which are most in need of proper diagnosis and therapy and which are most likely to be controlled by a pacemaker.

There is a related need, particularly with the advent of exercise-responsive pacemakers, to establish a pacing rate or rates best suited for a patient's individual physical condition and his anticipated range of activities. Cardiac output defines the pumping capability of the ventricles, and a primary determinant of cardiac output is heart rate. Accordingly, there is an increasing need to know cardiac output at different pacing rates at rest as well as during exercise. At present there is limited information on the subject of cardiac output versus pacing rate in pacemaker patients. Some studies conducted on normal subjects at rest indicate that cardiac output changes little before decreasing with an increase in pacing rate. However, in patients with impaired ventricles, a slight increase in pacing rate may cause a decrease in cardiac output. A survey of studies on this subject is included in a paper by Geddes et al. entitled "The Exercise-Responsive Cardiac Pacemaker," published in *IEEE Transactions on Biomedical Enoineerino BME* 31(12):763–770 (1984). This paper describes a three-phase relationship which was found to exist between cardiac output and pacing rate and includes a graphical illustration of the relationship, which is also illustrated in this application, in FIG. 6A, along with an additional curve showing the possibility of cardiac output remaining constant in Phase II of the resting state. Further information on this subject may be found in a paper by Fearnot et al., entitled "Control of Pacing Rate Using Venous Blood Temperature," on pages 69–72 of the 39th ACEMB Proceedings, Sept. 1986, and in an article by Wessale et al. in the May, 1988 issue of PACE. entitled "Cardiac Output Versus Pacing Rate at Rest and With Exercise in Dogs With AV Block."

Cardiac output depends on the heart rate, which is controlled by the pacemaker, and the stroke volume, which relies on the pumping capability of the ventricles. The pacing rate which results in maximum cardiac output for a given exercise level is the optimal pacing rate for that exercise level. Optimum pacing rates need to be determined for rest and exercise when a sensor-driven pacemaker is implanted. Unfortunately, the optimum pacing rate varies from patient to patient, because, among other reasons, stroke volume is dependent on the contractile status of the myocardium, and because patients have varying degrees of underlying cardiac disease. There is a need for an objective method of choosing optimum pacing rates, and it is believed that such an objective method requires a convenient way to obtain data on a particular patient's cardiac output over a range of pacing rates for each selected workload.

Another application of impedance-based sensors of stroke volume is in the detection of ventricular fibrillation. Such applications are likely to become widespread in the near future, particularly in automatic implantable cardioverter-defibrillators, which can save the life of a patient at risk of recurrent ventricular fibrillation by administering a defibrillating shock when needed. During ventricular fibrillation, stroke volume drops to essentially zero, and one would expect a corresponding drop in the pulsatile impedance change detected in the ventricle. This principle has been employed in a defibrillator designed for automatic actuation only when the mechanical activity and electrical activity of the ventricle both indicate a need for defibrillation. This defibrillator, described in U.S. Pat. No. 4,291,699 to Geddes et al., used a bipolar catheter-borne electrode pair to detect the cardiac electrogram and also to detect the pulsatile impedance change in the ventricle. The defibrillator delivered a shock only when both electrocardiographic and impedance criteria for fibrillation were met, reducing the probability of applying an inappropriate shock.

In a paper entitled "Optimal Spacing of Right Ventricular Bipolar Catheter Electrodes for Detecting Cardiac Pumping by an Automatic Implantable Defibrillator," *Med. Instrum.* 14:27 (1980), Tacker et al., using large-area, catheter-borne electrodes, evaluated five different spacings between bipolar electrodes and concluded that a 5 mm separation identified ventricular fibrillation more reliably than wider electrode separation. Our recent research in this area suggests, to the contrary, that the greater the separation between electrodes, the more rapidly the pulsatile impedance amplitude ratio decreases at the onset of fibrillation. Relatively closely spaced electrodes appear to be more susceptible to artifacts which may adversely affect the ability to reliably detect loss of stroke volume during fibrillation.

SUMMARY OF THE INVENTION

The present invention overcomes these and other disadvantages of the prior art by providing a novel system and method for measuring stroke volume based on a monopolar electrode configuration.

According to one aspect of the invention, such a system includes multiple monopolar electrodes axially spaced along the surface of the distal end of an impedance catheter, and a reference electrode adapted for positioning distant from the monopolar electrodes in a patient's body. The system further includes a monopolar means for supplying a drive signal and measuring impedance between each of the monopolar electrodes and the distant reference electrode.

Another aspect of the invention relates to a system for use in determining desired heart rate for a patient undergoing cardiac therapy. Such a system includes means for receiving heart rate data including multiple samples of a patient's heart rate during induced variations thereof at a particular workload. The system also includes monopolar impedance-based means for measuring the patient's stroke volume during said induced variations in heart rate, the monopolar means including means for measuring impedance between a monopolar electrode positioned in the patient's heart and a distant reference electrode. The receiving means and monopolar impedance-based means are coupled to a means for multiplying heart (or pacing) rate by stroke volume to obtain an impedance-based value proportional to the patient's cardiac output during the induced variations in heart rate.

According to a further aspect of the invention, detection of ventricular fibrillation is enhanced by an impedance-based method which includes measuring pulsatile impedance changes between a monopolar electrode disposed within a patient's heart and a distant reference electrode, and detecting the onset of fibrillation by recognition of a reduction of pulsatile impedance changes in excess of a predetermined amount, combined with absence of normal ventricular electrical activity for longer than a predetermined interval of time.

It is a general object of the present invention to provide an improved system and method of measuring stroke volume.

Another object is to accommodate changes in a particular patient's physical condition over time, such as changes in the nature of the contractility of the patient's ventricle as a result of changes in shape and contractility of the ventricle.

Another object of the invention is to accommodate changes in impedance catheter performance over time.

Yet another object of the invention is to enable reliable determination of the optimal pacing rate or rates best suited for a pacemaker patient's individual physical condition and his anticipated range of activities.

A still further object of the invention is to provide a more rapid and reliable method of detecting ventricular fibrillation.

These and other objects and advantages of the invention will become more apparent upon reading the following detailed description of the preferred embodiment in conjunction with the accompanying drawings.

DESCRIPTION OF THE PREFERRED EMBODIMENT

Figure 1:
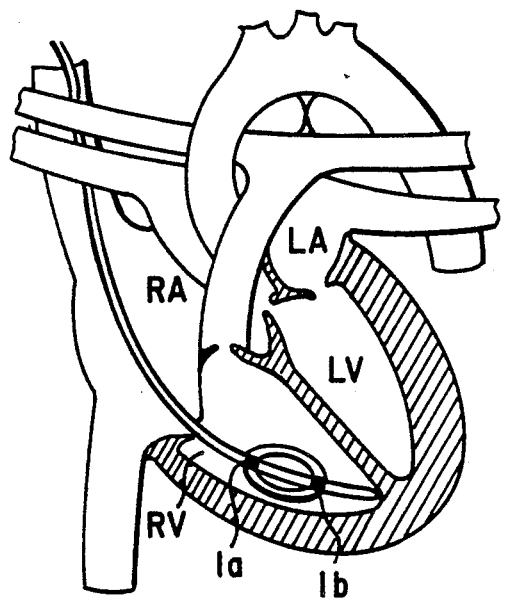
FIG. 1 is an illustration of the theoretical current flow from a bipolar right-ventricular (RV) catheter electrode.
Figure 2:
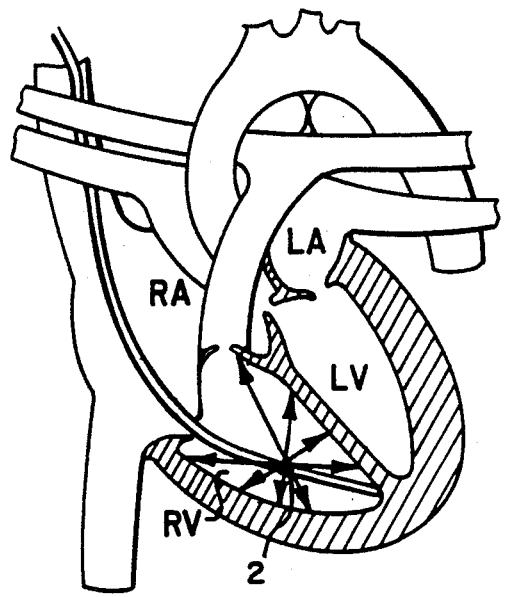
FIG. 2 is an illustration of the theoretical current flow from a monopolar right-ventricular (RV) catheter electrode.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 3:
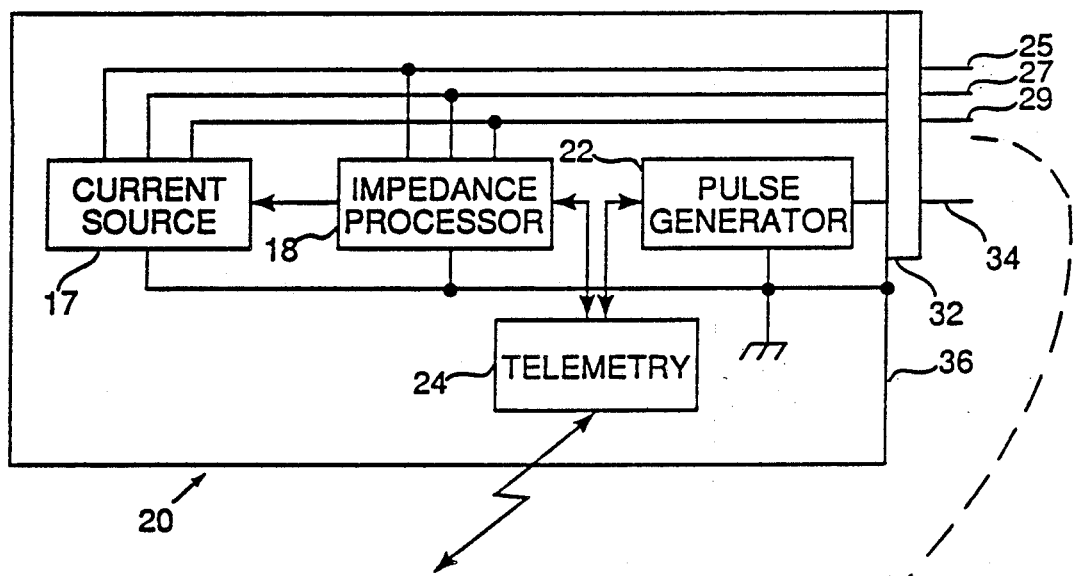
FIG. 3 is a block diagram of the preferred embodiment of the present invention, with an impedance catheter with multiple monopolar electrodes disposed in the right ventricle of the heart.
Figure 3:
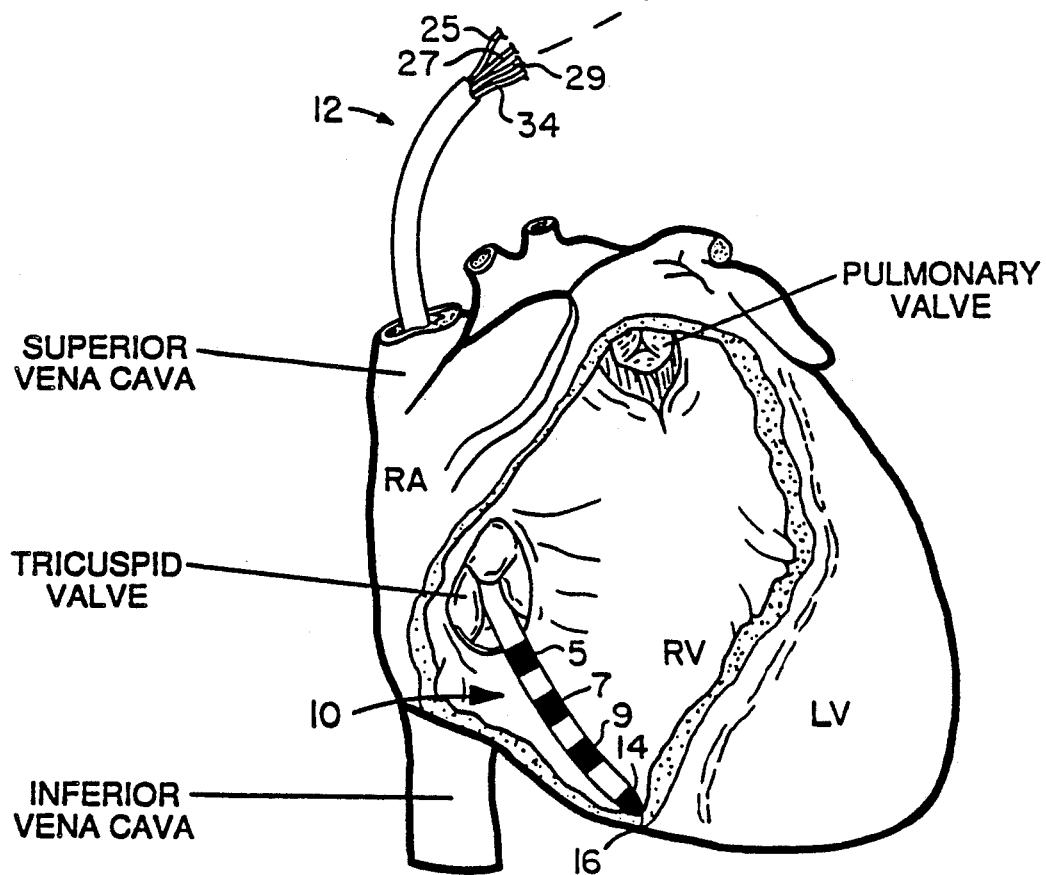

In the preferred embodiment of the present invention, multiple monopolar impedance-measurement electrodes, e.g., electrodes 5, 7 and 9 shown in FIG. 3, are provided on the distal end 10 of a transvenous lead 12 along with a stimulating electrode 14 at the tip 16 and are electrically connected to a current source 17 and impedance processor 18 incorporated within an implantable cardiac device 20 having a pulse generator 22 for supplying stimuli to electrode 14. The cardiac device may be a defibrillator, pacemaker or other type of therapeutic device. The monopolar electrodes 5, 7 and 9 are connected by separate electrical conductors 25, 27 and 29 which extend from the electrodes through pacing lead 12 to a connector 32 and therethrough to current source 17 and impedance processor 18. Likewise, a separate conductor 34 is provided from pulse generator 22 to stimulating electrode 14. Current source 17 is electrically connected between a selected one of the monopolar electrodes, via its associated conductor, and the device case or housing 36, which thus serves as the passive or indifferent electrode for a monopolar recording of right-ventricular impedance when the cardiac device is implanted and the combined impedance catheter and lead 12 is disposed with the monopolar electrodes 5, 7 and 9 in the right ventricle (RV). The impedance processor measures the voltage appearing across the selected one of the monopolar electrodes and the device case, which voltage is primarily a function of the impedance of the blood in the ventricle and secondarily a function of the significantly higher but relatively constant impedance of body tissue between the monopolar electrodes and the case. As a result, changes in impedance measured by the impedance processor are predominantly proportional to changes in ventricular blood impedance, which in turn are inversely proportional to changes in ventricular volume.

Figure 4:
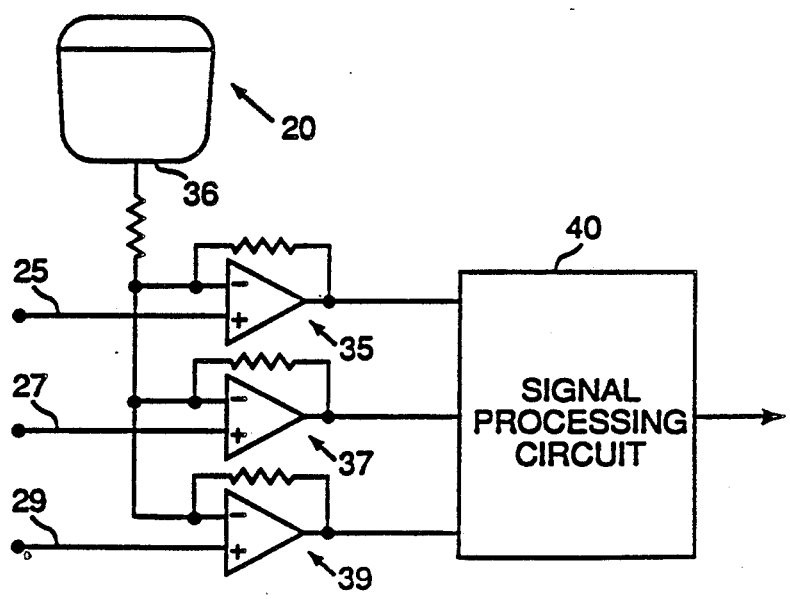
FIG. 4 is an illustration of the impedance processor shown in FIG. 3.
Figure 5:
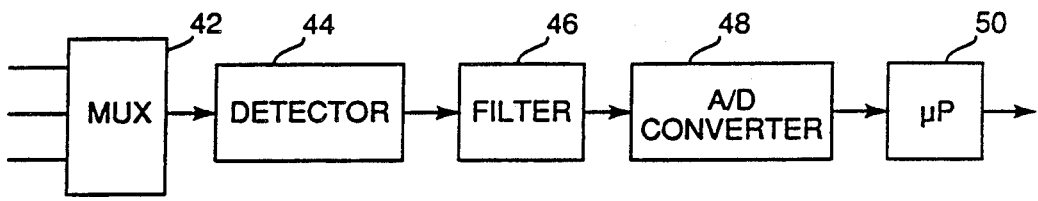
FIG. 5 shows further details of the impedance processor shown in FIG. 3.

Preferably current source 17 includes a single constant-current generator which is sequentially switched between selected monopolar electrodes at a rapid rate relative to the length of a cardiac cycle, and impedance processor 18 is switched between the selected conductors in synchronism with the switching of the current source connections. Impedance processor 18 includes individual buffer amplifiers 35, 37 and 39, as shown in FIG. 4, connected respectively to conductors 25, 27 and 29. Each buffer amplifier delivers a voltage proportional to that appearing between its associated monopolar electrode and case 36 to a signal processing circuit 40. Circuitry is provided within processing circuit 40 to obtain a weighted sum of the buffered impedance signals. A summing amplifier with individually variable gain for each input may be constructed with operational amplifier circuitry, or the function may be implemented with digital circuitry. With reference to FIG. 5, the signal processing circuit 40 preferably includes a multiplexer (MUX) 42 for selection of a particular buffered impedance signal to be supplied at a given time to an envelope detector or demodulator 44 the output of which is connected to a filter 46 and, in turn, to an A/D converter 48 and microprocessor 50 as shown in the drawing.

Changes in the amplitude of the output signal from detector 44 represent changes in ventricular impedance. Respiratory impedance artifacts are filtered out with a high-pass filter in filter 46, which is designed to pass only impedance signals corresponding to mechanical activity of the ventricle. Filter 46 may be of the analog type disclosed in U.S. Pat. No. 4,291,699 to Geddes et al., which is hereby incorporated by reference. Alternatively, the filter may be of a bandpass type which rejects both the carrier frequency and the lower respiratory frequencies. Such a filter preferably has a lower frequency cutoff which is discretely programmable via telemetry within the range of 0.01 to 1 Hz, for example, 0.01 Hz, 0.02 Hz, 0.05 Hz, 0.1 Hz, 0.2 Hz, 0.5 Hz, or 1.0 Hz. The upper frequency cutoff is fixed according to that necessary for a rejection of the current source carrier frequency in the range of 10 to 100 Hz. As a further alternative, signal processing circuit 40 may include a digital filter designed to perform the functions of filter 46. Microprocessor 50 is programmed to control signal sampling through MUX 42 and A/D converter 48, and includes an impedance algorithm for obtaining a weighted sum of samples from the individual monopolar electrodes on the catheter. The algorithm preferably includes a variable weighting factor for each monopolar electrode, and the impedance processor preferably includes a telemetry circuit 24 coupled to the microprocessor for communication with an external programmer. One of the advantages of such a configuration is that the weight to be accorded any particular electrode can be easily changed as desired by a clinician or attending physician, such as to make necessary adjustments to obtain the impedance change that best reflects stroke volume.

It is also contemplated that a single monopolar electrode may be selected to provide the impedance change that is most representative of stroke volume. Such a decision would typically be made by an attending physician in light of a patient's individual condition, as indicated, for example, by physical examination including comparison of data between the telemetered stroke volume and external indications of actual cardiac output or stroke volume. In this way, over the years that the cardiac device is implanted, it would be possible to accommodate any changes in the patient's heart or the natural changes as the catheter becomes fixed to the myocardium. Moreover, it provides a backup in case another selected electrode fails. The algorithm stored in the microprocessor preferably includes the capability to select an individual monopolar electrode in response to a signal from the external programmer. Most preferably, the algorithm is capable of selecting any one or more of the monopolar electrodes. Such capabilities may be implemented with the weighted-sum circuit by making the weighting factors continuously selectable between zero and unity, whereby any desired combination of the available impedance signals may be achieved.

As an alternative to sequential selection of monopolar electrodes, the current source in the cardiac device may be provided with a current source of different frequency for each of the monopolar electrodes. In this alternative embodiment, the impedance processor simultaneously receives and processes impedance signals at the various frequencies, and for this purpose includes appropriate circuitry for discriminating among the signals on the basis of frequency. For example, a separate detector 44 and filter 46 may be provided for each channel, with signal multiplexing being performed at the input to the A/D converter rather than at a detector input. The processed impedance signals are added using a weighted-sum circuit of the type described above.

A constant sinusoidal alternating current of typically 100 μA at 12 kHz (or higher) is suitable in the case of a current source of single frequency. In the alternative embodiment with a different frequency for each monopolar electrode, the frequencies should be established in bands above 12 kHz in which the impedance characteristics of interest are relatively constant with respect to frequency but in which sufficient frequency spacing is available for frequency discrimination by the impedance processor.

Telemetry circuit 24 is preferably provided with data and control lines for two-way communications with impedance processor 18 and pulse generator 22, and in pacemaker applications is preferably capable of transmitting heart rate and stroke volume information to an external programmer which includes means for multiplying heart (e.g., pacing) rate by stroke volume to obtain relative cardiac output and to generate a display of relative cardiac output as a function of pacing rate. This assists a clinician or attending physician in determining the optimal pacing rates at different exercise levels for each patient using the three-phase relationship and thereby ensures the greatest benefit from exercise-responsive pacing. In such an application, pulse generator 22 includes conventional circuitry for controlling and monitoring pacing rate in a programmable manner, and for communicating pacing rate data to telemetry circuit 24. Pulse generator 22 may include a separate microprocessor for rate control functions, as well as for programmable control of operating mode, pulse width and amplitude, or, alternatively, a single microprocessor may be programmed to perform these functions as well as the data processing functions of impedance processor 18. Pulse generator 22 also preferably includes conventional sense amplifier circuitry to enable the pacemaker to operate in the demand mode, and further includes programmable means for varying the sensitivity of the sense amplifier. The common processor described above advantageously includes, in addition to an algorithm for calculating stroke volume from impedance data, a multiplication algorithm for direct calculation of cardiac output.

The pacemaker rate control algorithm is preferably responsive to some physiological parameter indicative of exercise, and may cause an immediate switch from one optimal pacing rate to another upon detection of a change of state or may use the optimum pacing rates as target rates to be reached over an interval of time or in a manner determined by the algorithm in accordance with sensed physiological conditions. As described thus far, the disclosed pacemaker is suited for automatic rate control in response to stroke volume or cardiac output measured with the catheter-borne monopolar electrodes. Additional sensors would be required to adapt the pacemaker to respond to some physiological parameters, such as central venous blood temperature, body motion, and venous oxygen saturation.

Figure 6A:
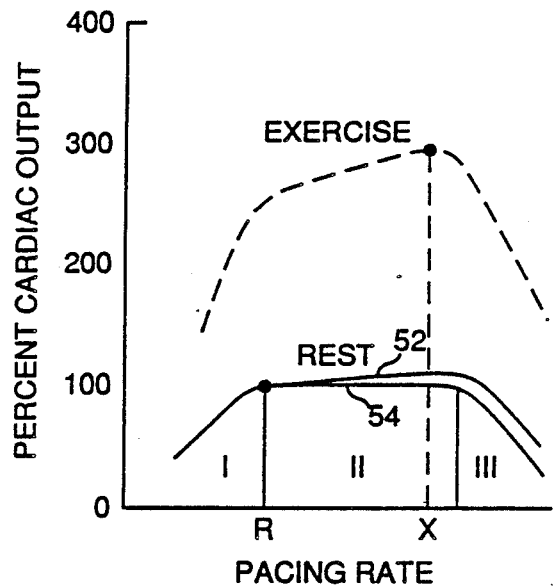
FIG. 6A shows the three-phase relationship between cardiac output and pacing rate in normal subjects.

The optimal pacing rate for a given exercise level is that rate which results in the maximum cardiac output. In hearts with normal, unimpaired ventricular function, the available data suggests that there are three phases to the relationship between cardiac output and pacing rate, as illustrated in FIG. 6A for rest and one level of exercise. Increases in rate produce corresponding increases in cardiac output at rest over a range identified as Phase I in the drawing. However, during the resting state, there is little (curve 52) or no (curve 54) increase in cardiac output for further increases in pacing rate. Hence, the pacing rate R at the transition from Phase I to Phase II is considered the optimum pacing rate during the resting state. For exercise with normal ventricles, three phases also exist. However, additional increase in cardiac output is achieved by increasing the pacing rate within the range of rates identified as Phase II. Therefore, the transition from Phase II to Phase III marks the optimum rate (X) for exercise. Increasing the pacing rate beyond rate X will result in decreased cardiac output. It is believed that a subject-specific optimum pacing rate exists for each constant exercise level for each patient, and that it may be possible to identify an optimum pacing rate for each patient at a particular workload by adjusting the patient's pacing rate and monitoring the effect on cardiac output while the patient undergoes treadmill or bicycle ergometer testing at a constant workload. Similarly, it should be possible to determine the optimum pacing rate for the same patient at a different exercise level by adjusting the treadmill or ergometer for a different required workload and repeating the test.

Figure 6B:
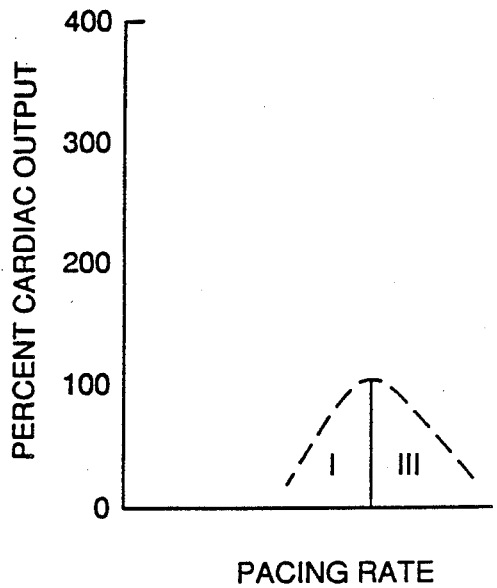
FIG. 6B shows the corresponding relationship for subjects with impaired ventricles.

Although a three-phase relationship appears to exist between cardiac output and pacing rate in healthy ventricles, Phase II may be narrow or absent when the ventricles are impaired, as illustrated by FIG. 6B. In such a case, the cardiac output initially increases and then decreases without leveling off as the pacing rate is varied from a low to a high value, and in this case the optimum pacing rate is that rate which corresponds to the peak of the curve.

As an aid to a clinician in identifying the optimum heart rate, an algorithm may be provided in the programmer or elsewhere which determines the derivative of cardiac output as a function of pacing rate as the pacing rate is increased, and automatically identifies the optimal heart rate for the patient as the rate beyond which the incremental increase in cardiac output for an incremental increase in pacing rate is less than a predetermined value. The predetermined value could be either a desired minimum rate of rise or a desired maximum rate of fall, and would be expected to be different for rest and exercise, consistent with the curves shown in FIG. 6A.

The presently preferred embodiment also includes the capability of identifying ventricular tachycardia and fibrillation. We have found that the greater the separation between impedance electrodes, the more rapidly the pulsatile impedance amplitude ratio decreases at the onset of fibrillation. The impedance ratio is defined as the pulsatile impedance during fibrillation divided by the pulsatile impedance before the onset of ventricular fibrillation. Our experiments to date indicate that a monopolar electrode configuration produces a dramatic reduction in the ratio of peak-to-peak impedance amplitude during fibrillation to the control level of the peak-to-peak impedance amplitude, the control level being the amplitude level prior to the onset of fibrillation. We observed a 79% reduction in the ratio from control to 10 seconds of fibrillation. Such data indicate that a monopolar catheter-borne electrode system minimizes the difficulties associated with artifacts such as respiratory and atrial artifacts, particularly when respiratory artifacts, which occur at a lower frequency than ventricular activity, are attenuated to the extent possible with filter circuitry.

Figure 7:
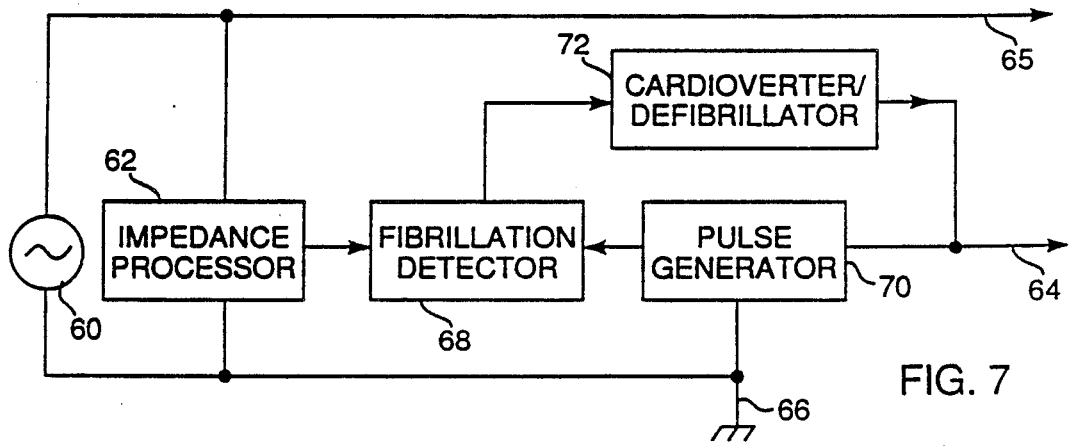
FIG. 7 is a block diagram of an embodiment of the present invention in which a cardioverter/defibrillator and a pacemaker are included within the implantable cardiac device.

Referring now to FIG. 7, a constant-current source 60 and impedance processor 62 connected between conductor 65 and the cardiac device case 66 enable measurement of ventricular stroke volume with a monopolar electrode lodged in the right ventricle, as described above. Impedance processor 62 is connected to one input of a fibrillation detector 68 which has another input connected to pulse generator 70 connected to the stimulating electrode through conductor 64. The same microprocessor which includes the impedance processing and rate control functions described above advantageously also includes an algorithm capable of identifying tachycardia and fibrillation in response to a predetermined combination of changes of ventricular electrical activity and mechanical pumping activity of the heart, as determined from ECG and impedance signals supplied from pulse generator 70 and impedance processor 62, respectively. An algorithm of this type is disclosed in the aforementioned U.S. Pat. No. 4,291,699 to Geddes et al., incorporated by reference herein. Such an algorithm includes the frequency of the QRS wave of the ECG and bipolar impedance-derived stroke volume as criteria for determination of fibrillation. Fibrillation detector 68 has an output connected to cardioverter/defibrillator 72, which is coupled via conductor 64 to the stimulating lead for delivery of a defibrillating shock upon detection of insufficient electrical activity combined with absence of ventricular pumping. If minimal pumping is detected by fibrillation detector 68, cardioverter/defibrillator 72 delivers a cardioversion, which is less intense than a defibrillating shock.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A multiple monopolar system for measuring the stroke volume of a patient's heart, comprising:
    an intracardiac impedance catheter having a distal end and a proximal end;
    a plurality of same-polarity-monopolar electrodes axially spaced along the surface of said distal end of said impedance catheter;
    a reference electrode adapted for positioning distant from said monopolar electrodes in the patient's body; and
    monopolar means for supplying a drive signal and measuring impedance between each of said monopolar electrodes and said distant reference electrode.

2. A multiple monopolar system for measuring the stroke volume of a patient's heart, comprising:
   an intracardiac impedance catheter having a distal end and a proximal end;
   a plurality of monopolar electrodes axially spaced along the surface of said distal end of said impedance catheter;
   a reference electrode adapted for positioning distant from said monopolar electrodes in the patient's body;
   monopolar means for supplying a drive signal and measuring impedance between each of said monopolar electrodes and said distant reference electrode;
   an implantable cardiac device having a conductive case which incorporates said reference electrode, said cardiac device including a pulse generator housed within said case, said case being attached to said proximal end of said catheter;
   a stimulating electrode disposed on said distal end of said catheter distal to said monopolar electrodes;
   a first electrical conductor connected to said stimulating electrode and extending therefrom within said catheter to said proximal end thereof;
   means for electrically connecting said pulse generator to said first electrical conductor; and
   a plurality of individual electrical conductors connected to respective ones of said monopolar electrodes and extending therefrom within said catheter to said proximal end thereof;
   wherein said monopolar means further includes a current source and an impedance processor housed within said case, and means for electrically connecting an output of said current source and an input of said impedance processor to each of said individual conductors.

3. The multiple monopolar system of claim 2 wherein said monopolar means further includes means for selecting the monopolar electrode whose output is determined to be most representative of stroke volume for a particular patient.

4. The multiple monopolar system of claim 2 wherein said monopolar means further includes means for switching said current source and said impedance processor sequentially between selected ones of said individual conductors; and
   wherein said impedance processor includes means for obtaining a weighted sum of signals appearing on said individual conductors from said monopolar electrodes.

5. The multiple monopolar system of claim 2 wherein said monopolar means further includes means for connecting said current source and said impedance processor simultaneously to said individual conductors.

6. The multiple monopolar system of claim 5 wherein said current source includes means for driving said individual conductors at different frequencies, and wherein said impedance processor includes means for discriminating on the basis of frequency between signals appearing on said individual conductors from said monopolar electrodes.

7. A multiple monopolar method of measuring the stroke volume of a patient's heart, comprising the steps of:
   introducing into the patient's heart an impedance catheter having a plurality of same-polarity-monopolar electrodes axially spaced along the surface of one end;
   positioning a reference electrode distant from said monopolar electrodes in the patient's body; and
   supplying a drive signal and measuring impedance between each of said monopolar electrodes and said distant reference electrode for measuring the stroke volume of said heart.

8. A multiple monopolar method of measuring the stroke volume of a patient's heart, comprising the steps of:
   introducing into the patient's heart an impedance catheter having a plurality of monopolar electrodes axially spaced along the surface of one end;
   positioning a reference electrode distant from said monopolar electrodes in the patient's body;
   supplying a drive signal and measuring impedance between each of said monopolar electrodes and said distant reference electrode;
   wherein said supplying step is performed with a current source and an impedance processor housed within a case of an implantable cardiac device, said cardiac device including a pulse generator housed within said case, said case being attached to said proximal end of said catheter;
   wherein said catheter includes a stimulating electrode disposed on said distal end thereof distal to said monopolar electrodes, and an electrical conductor connected to said stimulating electrode and extending therefrom within said catheter to said proximal end thereof; and
   wherein said supplying step further includes electrically connecting an output of said current source and an input of said impedance processor to each of a plurality of individual electrical conductors connected to respective ones of said monopolar electrodes and extending therefrom within said catheter to said proximal end thereof for measuring the stroke volume of said heart.

9. A multiple monopolar method of claim 8, further comprising the step of selecting the monopolar electrode whose output is determined to be most representative of stroke volume for a particular patient.

10. The multiple monopolar method of claim 8, further comprising the steps of:
    switching said current source and said impedance processor sequentially between selected ones of said individual conductors; and
    obtaining a weighted sum of signals appearing on said individual conductors from said monopolar electrodes.

11. The multiple monopolar method of claim 8, further comprising the step of connecting said current source and said impedance processor simultaneously to said individual conductors.

12. The multiple monopolar method of claim 11, further comprising the step of driving said individual conductors at different frequencies, and discriminating on the basis of frequency between signals appearing on said individual conductors from said monopolar electrodes.

13. A system for use in determining desired heart rate for a patient undergoing cardiac therapy, comprising:
    means for receiving heart rate data including multiple samples of the patient's heart rate during induced variations thereof at a particular workload;
    monopolar impedance-based means for measuring the patient's stroke volume during said induced variations in heart rate, said monopolar means including means for measuring impedance between a monopolar electrode positioned in the patient's heart and a distant reference electrode; and means coupled to said receiving means and said monopolar impedance-based means for multiplying said heart rate data by said measured stroke volume to obtain an impedance-based value proportional to the patient's cardiac output during said induced variations in heart rate.

14. The system of claim 13, further comprising an implantable pacemaker having means for adjustably controlling the patient's heart rate, said pacemaker including telemetry means for transmitting heart rate data to said receiving means.

15. The system of claim 14, further comprising means for analzing the relationship between the impedance-based value proportional to cardiac output and the patient's heart rate and identifying therefrom the desired heart rate for the patient at said particular workload as the heart rate beyond which the incremental increase in cardiac output for an incremental increase in heart rate is less than a predetermined value.

16. The system of claim 15 wherein said distant reference electrode is located on said pacemaker.

17. A method of determining desired heart rate for a patient undergoing cardiac therapy, comprising the steps of:

inducing variations in the patient's heart rate at a particular workload;

measuring the patient's heart rate during said induced variations in heart rate;

measuring the patient's stroke volume during said induced variations in heart rate, said step of measuring stroke volume including measuring impedance between a monopolar electrode positioned in the patient's heart and a distant reference electrode; and multiplying measured heart rate by measured stroke volume to obtain an impedance-based value proportional to the patient's cardiac output during said induced variations in heart rate.

18. The method of claim 17 wherein said step of measuring the patient's heart rate is performed with an implantable pacemaker of the type having telemetry means for transmitting heart rate data transcutaneously, and wherein said inducing step includes varying the rate of said pacemaker while maintaining a fixed workload.

19. The method of claim 18, further comprising the step of analyzing the relationship between the impedance-based value proportional to cardiac output and the patient's heart rate and identifying therefrom the desired heart rate for the patient at said particular workload as the heart rate beyond which the incremental increase in cardiac output for an incremental increase in heart rate is less than a predetermined value.

20. The method of claim 19 wherein said distant reference electrode is located on said pacemaker.

21. An impedance-based method of detecting ventricular fibrillation of a heart, comprising the steps:

measuring pulsatile impedance changes between a monopolar electrode disposed within said heart and a reference electrode outside said heart; and detecting the onset of fibrillation by recognition of a reduction of pulsatile impedance changes in excess of a predetermined amount, and the absence of electrical activity for longer than a predetermined interval of time.

22. The method of claim 21 wherein said measuring step is performed with said monopolar electrode centrally positioned within the right ventricle.

23. The method of claim 22 wherein said detecting step includes recognizing a rate of reduction in excess of a predetermined rate characteristic of said heart.

24. A multiple monopolar system for measuring the stroke volume of a patient's heart, comprising:

an intracardiac impedance catheter having a distal end and a proximal end;

a plurality of monopolar electrodes axially spaced along the surface of said distal end of said impedance catheter;

an extracardial reference electrode; and monopolar means for supplying a drive signal and measuring impedance between each of said monopolar electrodes and said extracardial reference electrode.

25. The multiple monopolar system of claim 24, wherein said monopolar means includes means for obtaining a weighted sum of signals from said monopolar electrodes.

26. A multiple monopolar method of measuring the stroke volume of a patient's heart, comprising the steps of:

introducing into the patient's heart an impedance catheter having a plurality of monopolar electrodes axially spaced along the surface of one end;

positioning a reference electrode outside the patient's heart; and supplying a drive signal and measuring impedance between each of said monopolar electrodes and said reference electrode outside the patient's heart for measuring the stroke volume of said heart.

27. The multiple monopolar method of claim 26, further comprising the step of obtaining a weighted sum of signals from said monopolar electrodes.

* * * * *